United States Patent

Cauwet et al.

[11] Patent Number: 5,853,708
[45] Date of Patent: Dec. 29, 1998

[54] COSMETIC COMPOSITIONS CONTAINING AT LEAST ONE ANIONIC SURFACTANT OF ALKYLGALACTOSIDE URONATE TYPE AND AT LEAST ONE SYNTHETIC HYDROCARBON OIL

[75] Inventors: Daniele Cauwet, Paris; Claude Dubief, Le Chesnay, both of France

[73] Assignee: L'Oreal, Paris, France

[21] Appl. No.: 961,034

[22] Filed: Oct. 30, 1997

Related U.S. Application Data

[63] Continuation of Ser. No. 553,429, Nov. 28, 1995, abandoned.

[30] Foreign Application Priority Data

Jun. 1, 1993 [FR] France ................. 93 06532

[51] Int. Cl.⁶ .................. A61K 7/00; A61K 7/07
[52] U.S. Cl. .............. 424/70.22; 424/70.1; 424/70.19
[58] Field of Search ............ 424/70.1, 70.22, 424/70.19

[56] References Cited

U.S. PATENT DOCUMENTS 5,501,812  3/1996  Vermeer ............... 252/174.17

FOREIGN PATENT DOCUMENTS 0 550 276  3/1993  European Pat. Off. .
0 532 370  7/1993  European Pat. Off. .

*Primary Examiner*—Sally Gardner-Lane
*Attorney, Agent, or Firm*—Jacobson, Price, Holman & Stern, PLLC

[57] ABSTRACT

Cosmetic compositions containing in an aqueous medium an alkylgalactoside uronate and a synthetic hydrocarbon oil and their use in the treatment or washing of keratinous materials. The alkylgalactoside uronate is based on formula (I):

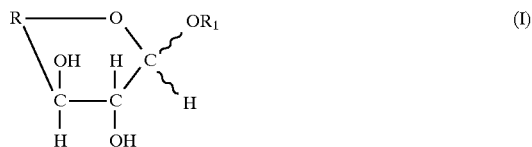

$R_1$ is a $C_8$–$C_{22}$ alkyl;
R is (i) or (ii):

>CH—CH(OH)—CO₂R₂     (i)

—CH(OH)—CH—CO₂R₂     (ii)

with the carbon carrying the hydroxyl group being linked to the endocyclic oxygen atom;

$R_2$ is hydrogen, an alkaline metal, an alkaline-earth metal or a quaternary ammonium group.

18 Claims, No Drawings

COSMETIC COMPOSITIONS CONTAINING AT LEAST ONE ANIONIC SURFACTANT OF ALKYLGALACTOSIDE URONATE TYPE AND AT LEAST ONE SYNTHETIC HYDROCARBON OIL

This application is a continuation of application Ser. No. 08/553,429, filed Nov. 28, 1995, now abandoned, which is a 371 of PCT/FR94/00632, filed May 31, 1994.

The invention relates to cosmetic compositions containing at least one anionic surfactant of alkylgalactoside uronate type and one synthetic hydrocarbon oil and to their use in treating keratinous substances.

Compositions for washing the hair or the skin are generally formulated from anionic or nonionic surfactants or their mixtures, optionally in the presence of amphoteric surfactants.

Compositions for washing the hair which contain only these surfactants do not lead to good cosmetic properties; in particular, the disentangling of wet hair is difficult and the volume and the quality of the lathers are unsatisfactory.

It has been proposed to add natural or synthetic oils to these washing compositions in order to improve the cosmetic properties.

However, the lathering ability of such compositions and the quality of the lathers remain unsatisfactory.

Anionic surfactants of alkylgalactoside uronate type have already been recommended in washing compositions for the hair. They have been described in Patent Application EP 0,532,370.

The Applicant Company has just surprisingly discovered that the combination, in washing and/or treating compositions for keratinous substances, of an anionic surfactant of alkylgalactoside uronate type and of a synthetic hydrocarbon oil confered on these compositions improved disentangling properties for wet hair.

Moreover, the combination in accordance with the present invention makes it possible to obtain a copious, compact and very gentle lather.

In addition, the Applicant Company has observed that cosmetic compositions containing such a combination confer good cosmetic properties, such as softness and a pleasant feel.

The subject of the present invention is therefore cosmetic compositions containing at least one anionic surfactant of alkylgalactoside uronate type and one synthetic hydrocarbon oil.

Another subject of the invention consists of the use of these compositions for treating and/or washing keratinous substances such as the hair or the skin.

Another subject relates to a cosmetic treatment process for the hair or for the skin by means of the compositions of the invention; washing and treatment processes for the hair being preferred.

The cosmetic compositions according to the invention contain, in a cosmetically acceptable aqueous medium:
(A) at least one anionic surfactant of alkylgalactoside uronate type of formula:

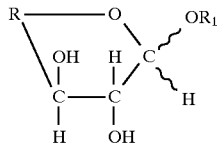

(I)

in which:

$R_1$ denotes a linear or branched alkyl radical containing 8 to 22 carbon atoms, R denotes a group
  (i) >CH—CH(OH)—CO$_2$R$_2$ or
  (ii) —CH(OH)—CH—CO$_2$R$_2$, in which the carbon carrying the hydroxyl group is connected to the endocyclic oxygen atom; $R_2$ being a hydrogen, an alkali metal, an alkaline-earth metal or a quaternary ammonium group which is unsubstituted or substituted by alkyl or hydroxyalkyl radicals or an ammonium group derived from amino acids, (B) and at least one synthetic hydrocarbon oil.

Anionic surfactants of alkylgalactoside uronate type of formula (I) are known and may be prepared according to the processes described in Patent Application EP-A-0,532,370 [sic].

The alkali metal is in particular sodium or potassium and the alkaline-earth metal is preferably magnesium. Mention may be made, as quaternary ammonium salts, of the salts of ammonia, of triethanolamine, of monoethanolamine, of 2-amino-2-methyl-1,3-propanediol or of 2-methyl-2-amino-1-propanol; the amino acid is in particular histidine, arginine or lysine.

Use is preferably made of the compounds of formula (I) in which the $R_1$ radical denotes a $C_8$–$C_{14}$ alkyl and more particularly the decyl radical.

Use is in particular made of the following compounds:

Sodium decyl α-D-galactopyranoside uronate:

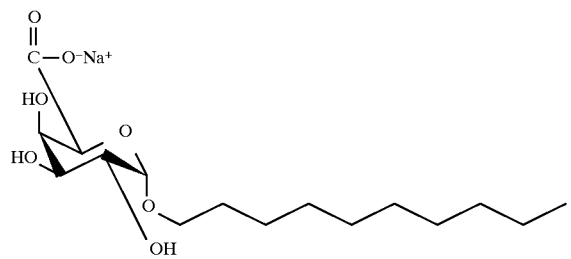

Sodium decyl β-D-galactopyranoside uronate:

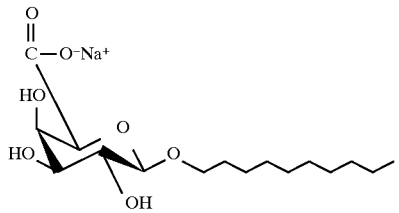

Sodium decyl α-D-galactofuranoside uronate:

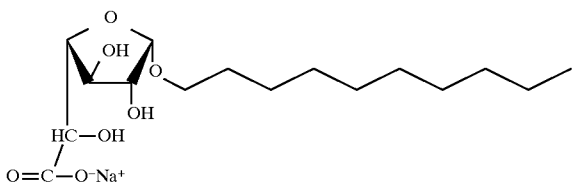

Sodium decyl β-D-galactofuranoside uronate:

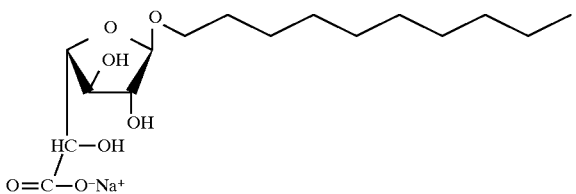

The synthetic hydrocarbon oils are preferentially poly-α-olefins and in particular:

a) of hydrogenated or nonhydrogenated polybutene type and preferably hydrogenated or nonhydrogenated polyisbutene [sic] type;

use is preferably made of isobutylene oligomers with a molecular weight of less than 1000 and their mixtures with polyisobutylenes with a molecular weight greater than 1000 and preferably between 1000 and 15,000; these products are sold, for example, by the company Amoco under the name Indopol, by the company Presperse under the names Permethyl 99A, 101A, 102A, 104A and 106A, or by the company ICI under the name Arlamol HD;

b) of hydrogenated or nonhydrogenated polydecene type; such products are sold, for example, by the company Ethyl Corporation under the names [sic] Ethylflo and by the company ICI under the names [sic] Arlamol PAO.

The alkylgalactoside uronates of formula (I) are used in the compositions in accordance with the invention in proportions preferably of between 0.5 and 30% by weight with respect to the total weight of the composition.

The hydrocarbon oils are used in the compositions of the invention in proportions preferably of between 0.1 and 20% by weight with respect to the total weight of the composition.

The compositions in accordance with the invention can additionally contain a thickening agent and/or a suspending agent for the oil such as fatty acid alkalnolamides [sic], poly(acrylic acid)s, cellulose derivatives, esters of fatty acids and of polyethylene glycol, crosslinked copolymers of acrylamide and of a monomer chosen from ammonium acrylate, partially or completely neutralized 2-acrylamido-2-methylpropanesulfonic acid or methacryloyloxyethyltrimethylammonium chloride; polyetherurethanes or crosslinked methyl vinyl ether-maleic acid copolymers.

Mention may also be made, as suspending agent for the oil, of the compounds chosen from
a) those of formula:

$$R_3X \quad (II)$$

in which $R_3$ is an aliphatic radical with a long carbon chain, optionally interrupted by one or a number of oxygen atoms, and X is a carboxylic, sulfuric or phosphoric acid residue or a radical derived from a carboxylic acid or from an amide; these compounds of formula (II) are chosen from those in which:

(i) $R_3$ is a $C_{11}$–$C_{21}$ alkyl or alkenyl radical;
and X is
  a COOA group where A is a mono- or polyhydroxyalkyl radical derived from a $C_2$–$C_3$ polyol or a $CH_2CH_2SO_3M$ radical;
  a $CO(OCH_2CH_2)_kOH$ group where k has a value of between 2 and 150;
  a group $$COOCH_2—CH—(OCH_2CH_2)_kOH,$$
$$\quad\quad\quad\quad CH_3$$

where k has a value of between 2 and 150, it being possible for the free OH functional groups of the groups defined above to be esterified with an acid R'COOH where R' is a $C_{11}$–$C_{21}$ alkyl or alkenyl;
  a $CONR_4R_5$ group where $R_4$ and $R_5$ represent hydrogen or $C_1$–$C_4$ hydroxyalkyl, at least one representing $C_1$–$C_4$ hydroxyalkyl;
  an $OSO_3M$ or $1/3PO_4^{3-}M_3$ group where M represents an alkali metal, ammonium or a $C_1$–$C_4$ alkanolamine residue;

(ii) $R_3$ denotes an $R_6O(C_2H_4O)_lCH_2$ radical and X denotes a COOM group where M has the meaning indicated above, $R_6$ denoting a $C_{12}$–$C_{14}$ alkyl radical and l a whole or decimal number between 2.5 and 10, or else $R_6$ denotes oleyl and l varies from 2 to 9 or alternatively $R_6$ denotes $(C_8$–$C_9)$alkylphenyl and l varies from 4 to 8, or the derivatives in which $R_6$ denotes a $(C_{12}$–$C_{16})$alkyl group and X a $CONR_4R_5$ group; in which $R_4$ and $R_5$ have the same meaning as that indicated above and l has a value from 1 to 3 inclusive;

b) amine oxides of formula:

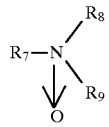

in which $R_7$ denotes a $C_{16}$–$C_{22}$ alkyl group and $R_8$ and $R_9$, which are identical or different, represent a $C_1$–$C_4$ alkyl or $C_1$–$C_4$ hydroxyalkyl group;

c) biopolysaccharides chosen from the xanthan gums and the scleroglucans.

If the compositions according to the invention are not used for washing keratinous substances, the concentration of anionic surfactants of formula (I) is between 1 and 10% and more particularly between 1 and 5% by weight with respect to the total weight of the composition. These compositions are used in particular as compositions to be rinsed or not to be rinsed, applied before or after shampooing, dyeing, bleaching, perming or hair straightening or in bleaching, dyeing, perming or hair-straightening compositions.

When the compositions according to the invention are washing compositions, they contain the surfactants of formula (I) in a concentration of between 4 and 50% by weight and preferably between 8 and 40% by weight with respect to the total weight of the composition.

The compositions can furthermore contain additional surfactants of anionic, nonionic, amphoteric, zwitterionic or cationic nature.

Among the anionic surfactants, there may be mentioned the alkali metal salts, the ammonium salts, the amine salts, the aminoalcohol salts or the magnesium salts of the following compounds: the fatty acids, alkyl sulfates, alkyl ether sulfates, alkylamidoether sulfates, alkylarylpolyether sulfates or monoglyceride sulfates; the alkylethersulfonates, alkylsulfonates, alkylamidesulfonates, alkylarylsulfonates, olefinsulfonates or paraffinsulfonates; the alkylsulfosuccinates, the alkylethersulfosuccinates or the alkylamidesulfosuccinates; the alkylsulfosuccinamates; the acylglutamates; the alkylsulfoacetates; the alkyl ether phosphates; the acylsarcosinates; the N-acyltaurates; or the isethionates.

The alkyl or acycl [sic] radical of these various compounds generally consists of a carbon chain containing from 10 to 20 carbon atoms.

It is also possible to use weakly anionic surfactants, such as the polyoxyalkylenated alkyl amide or alkyl ether carboxylic acids, such as those containing 2 to 50 ethylene oxide groups.

The nonionic surfactants are more particularly chosen from the polyethoxylated or polypropoxylated alcohols, α-diols or alkylphenols or fatty acids, with a fatty chain containing 8 to 18 carbon atoms, the number of ethylene oxide or propylene oxide groups being between 2 and 50 and the number of glycerol groups being between 2 and 30 [sic].

It is more particularly possible to mention the copolymers of ethylene oxide and of propylene oxide; the condensates of ethylene oxide and of propylene oxide with fatty alcohols; the polyethoxylated fatty amides having preferably 2 to 30 mol of ethylene oxide; the polyethoxylated fatty amines having preferably 2 to 30 mol of ethylene oxide; the oxyethylenated fatty acid esters of sorbitan having preferably 2 to 30 mol of ethylene oxide; the fatty acid esters of sugar [sic], the fatty acid esters of polyethylene glycol, the fatty acid esters of glycols; or the amine oxides such as the oxides of $(C_{10}-C_{14})$alkylamines or of N-acylamidopropylmorpholine.

The preferred amphoteric or zwitterionic surfactants are the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the $(C_8-C_{20})$ alkylbetaines, the sulfobetaines, the $(C_8-C_{20})$alkylamido $(C_1-C_6)$alkylbetaines or the $(C_8-C_{20})$alkylamido $(C_1-C_6)$ alkylsulfobetaines.

It is also possible to mention the alkylpeptides or the alkylimidazolium betaines.

Among the amine derivatives, there may be mentioned the products marketed under the name Miranol, such as those described in patents U.S. Pat. Nos. 2,528,378 and 2,781,354 or listed in the CTFA dictionary, 3rd edition, 1982, under the names of Amphocarboxyglycinates or of Amphocarboxypropionates.

The cationic surfactants are chosen from the quaternary ammonium salts, such as the $(C_8-C_{22})$ alkyltrimethylammonium halides, the $(C_8-C_{22})$ dialkyldimethylammonium halides or the $(C_8-C_{22})$ alkyldimethylhydroxyethylammonium halides.

The additional cosurfactants can represent up to 50% of the total weight of the surfactants present in the composition.

The pH of the compositions which is [sic] in accordance with the invention is generally between 2 and 10.5 and more particularly between 3 and 8.

Insofar as the cosmetically acceptable medium of the composition according to the invention is an aqueous medium, it may consist solely of water or of a mixture of water and of a cosmetically acceptable solvent, such as $C_1-C_4$ lower alcohols, such as ethanol, isopropanol or n-butanol; alkylene glycols, such as propylene glycol, or glycol ethers.

The compositions according to the invention can be provided in the form of more or less thickened liquids, gels, emulsions (milks or creams), aqueous/alcoholic lotions, dispersions, aerosol foams or solid bars.

The compositions are, for example, emollient lotions, milks or creams, lotions, milks or creams for caring for keratinous substances, make-up removal creams or milks, foundation bases, antisun lotions, milks or creams, lotions, milks or creams for artificial tanning, shaving creams or foams, aftershave lotions, face masks, make-up products for the eyes, colors and foundations for the face, nail varnishes, shampoos, bath or shower products, compositions to be rinsed or not to be rinsed, to be applied before or after shampooing, dyeing, bleaching, perming or hair straightening, or compositions for dyeing, bleaching, perming or straightening the hair.

The compositions in accordance with the invention can also contain, in addition, various additives such as foam reinforcers, sequestering agents, fragrances, electrolytes, fatty substances, such as fatty alcohols, ceramides, mineral, vegetable or animal oils or mineral, vegetable, animal or synthetic waxes, UV screening agents, agents for combating free radicals, pearlescence agents, biocides, antibacterials, antidandruff agents, antiseborrheic agents, antiparasitic agents, repellents, dyes, pigments, oxidizing agents, reducing agents, moisturizers, anionic and nonionic polymers, vitamins or α-hydroxy acids.

The process for washing and/or for conditioning the keratinous substances and in particular the hair or the skin in accordance with the invention consists in applying at least one composition as defined above to these substances, this application optionally being followed by a stage of rinsing with water.

The washing compositions can be used as a shampoo but also as a shower gel for washing the hair and the skin, in which case they are applied to the wet skin and hair, which are rinsed after application.

When the compositions are used for conditioning the hair, they are applied to the wet hair, after which it may either be dried or, after an exposure time of 1 to 10 minutes, rinsed with water. It is observed that the wet hair disentangles readily.

The examples which follow serve to illustrate the invention without, however, having a limiting nature.

EXAMPLE 1

SHAMPOO

| | |
|---|---|
| Sodium decyl D-galactoside uronate | 10 g M [sic] |
| Sodium lauryl ether sulfate ($C_{12}/C_{14}$ 70/30) containing 2.2 EO as a 28% aqueous solution sold under the name of Empicol ESB/3 FL by Marchon | 10 g AM |
| Isoicosane sold under the name of Permethyl 10 2 A by Creations Couleurs | 2 g |
| Hydroxypropyl guar gum sold under the name of Jaguar HP 60 by Meyhall | 0.75 g AM |
| Dyes, fragrance, preservative | q.s. for |
| water | 100 g |
| pH adjusted to 7 with NaOH | |

Appearance: opalescent and viscous

EXAMPLE 2

CONDITIONER

| | |
|---|---|
| Sodium decyl D-galactoside uronate | 4 g |
| Heptamethylnonane sold under the name of Arlamol HD by ICI | 10 g |
| Crosslinked poly(acrylic acid) sold under the name of Carbopol | 1.6 g AM |

-continued

| | |
|---|---|
| 980 by the Company Goodrich | |
| Dyes, fragrance, preservative | q.s. for |
| water | 100 g |
| pH adjusted to 5 with NaOH | |

The composition exists in the form of a white and viscous cream.

EXAMPLE 3

FOAM BATH

| | |
|---|---|
| Sodium decyl D-galactoside uronate | 20 g AM |
| Sodium N-cocoamidoethyl-N-(ethoxy-carboxymethyl)glycinate | 10 g AM |
| Heptamethylnonane sold under the name of Arlamol HD by ICI | 5 g |
| Oxyethylenated and oxypropylenated diurethane of alcohols ($C_{16}/C_{18}$) sold under the name of Dapral T 212 by the company Akzo | 2.5 g |
| Dyes, fragrance, preservative | q.s. for |
| water | 100 g |
| pH adjusted to 8 with NaOH | |

The composition exists in the form of an opalescent and slightly viscous liquid.

We claim:

1. Cosmetic composition comprising, in a cosmetically acceptable aqueous medium:

(A) between 0.5 and 30% by weight of at least one anionic surfactant of alkylgalactoside uronate type of formula:

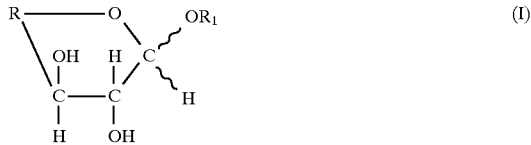

in which:

$R_1$ denotes a linear or branched $C_8$–$C_{22}$ alkyl radical

R denotes a group (i) CH—CH(OH)—$CO_2R_2$ or (ii) —CH(OH)—CH—$CO_2R_2$, in which the carbon carrying the hydroxyl group is connected to the endocyclic oxygen atom; $R_2$ denotes a hydrogen, an alkali metal or an alkaline-earth metal or a quaternary ammonium group which is unsubstituted or substituted by alkyls or hydroxyalkyls; and (B) between 0.1 and 20% by weight of at least one synthetic hydrocarbon oil selected from the group consisting of:

hydrogenated and non-hydrogenated polyisobutenes; and hydrogenated and non-hydrogenated polydecenes.

2. Composition according to claim 1, wherein, in formula (I), the radical $R_2$ denotes sodium or potassium; magnesium; or the quaternary ammonium group derived from ammonia, triethanolamine, monoethanolamine, 2-amino-2-methyl-1,3-propanediol, 2-methyl-2-amino-1-propanol, histidine, arginine or lysine.

3. Composition according to claim 1 wherein the compound of formula (I) is chosen from those in which $R_1$ denotes a $C_8$–$C_{14}$ alkyl.

4. Composition according to claim 1, wherein the compounds of formula (I) are chosen from those in which $R_1$ denotes a decyl radical.

5. Composition according to claim 4, wherein the compound of formula (I) is chosen from:

sodium decyl α-D-galactopyranoside uronate
sodium decyl β-D-galactopyranoside uronate
sodium decyl α-D-galactofuranoside uronate
sodium decyl β-D-galactofuranoside uronate.

6. Composition for conditioning keratinous substances according to claim 1, wherein the concentration of anionic surfactants of formula (I) is between 1 and 10% by weight with respect to the total weight of the composition.

7. Composition according to claim 1 wherein it further containing an additional anionic, nonionic, amphoteric or cationic cosurfactant in a proportion ranging up to 50% of the total weight of surfactants.

8. Washing composition according to claim 7, wherein the additional anionic cosurfactant is chosen from alkali metal salts, ammonium salts, amine salts, diaminoalcohols or magnesium salts of the compounds: fatty acids; alkyl sulfates, alkyl ether sulfates, alkylamidoether sulfates, alkylarylpolyether sulfates, monoglyceride sulfates or alkylamide sulfates; alkylsulfonates, alkylethersulfonates, alkylsulfosuccinates, alkylethersulfosuccinates or alkylamidesulfosuccinates; acylglutamates; alkylsulfosuccinamates; alkylsulfoacetates; alkyl ether phosphates; acylsarcosinates; N-acyltaurates; or isethionates; an alkyl or acyl radical consisting of a carbon chain containing from 10 to 20 carbon atoms or polyoxyalkylenated alkyl amide or alkyl ether carboxylic acids.

9. Washing composition according to claim 7, wherein the nonionic cosurfactant is chosen from alcohols, α-diols or alkylphenols; polyethoxylated or polypropoxylated fatty acids, with a fatty chain containing 8 to 18 carbon atoms, the number of ethylene oxide or propylene oxide groups being between 2 and 50 and the number of glycerol groups being between 2 and 30; copolymers of ethylene oxide and of propylene oxide; condensates of ethylene oxide and of propylene oxide with fatty alcohols; polyethoxylated fatty amides; polyethoxylated fatty amines; fatty acid esters of sugar; fatty acid esters of polyethylene glycol; fatty acid esters of glycols; or the amine oxides.

10. Composition according to claim 7, wherein the additional amphoteric or zwitterionic cosurfactant is chosen from the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the ($C_8$–$C_{20}$) alkylbetaines; the sulfobetaines, the ($C_8$–$C_{20}$)alkylamido ($C_1$–$C_6$)alkylbetaines or the ($C_8$–$C_{20}$)alkylamido($C_1$–$C_6$) alkylsulfobetaines; the alkylpeptides; or the alkylimidazoliumbetaines.

11. Washing composition according to claim 7, wherein the additional cationic cosurfactant is chosen from the quaternary ammonium salts.

12. Composition according to claim 1 wherein further containing a thickening agent and/or a suspending agent for the synthetic hydrocarbon oil.

13. Composition according to claim 12, wherein the thickening agent and/or the suspending agent is chosen from fatty acid alkanolamides; poly(acrylic acid)s; cellulose compounds; esters of fatty acids and of polyethylene glycol; crosslinked copolymers of acrylamide and of a monomer chosen from ammonium acrylate, 2-acrylamido-2-methylpropanesulfonic acid or methacryloyloxyethyltrimethylammonium chloride; polyetherurethanes; or crosslinked methyl vinyl ethermaleic acid copolymers.

14. Composition according to claim 12, wherein the suspending agent for the synthetic hydrocarbon oil is chosen from the following compounds a) compounds of formula:

$$R_3X \quad (II)$$

where $R_3$ is an aliphatic radical, optionally interrupted by one or a number of oxygen atoms, and X is a carboxylic, sulfuric or phosphoric acid residue or a radical derived from a carboxylic acid or from an amide;

b) amine oxides of formula

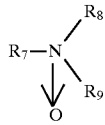

in which $R_7$ denotes a $C_{16}$–$C_{22}$ alkyl and $R_8$ and $R_9$, which are identical or different, represent a $C_1$–$C_4$ alkyl or $C_1$–$C_4$ hydroxyalkyl;

c) biopolysaccharides.

15. Composition according to claim 1, wherein the cosmetically acceptable medium consists of water or a mixture of water and of a cosmetically acceptable solvent.

16. Composition according to claim 1, wherein it is provided in the form of a more or less thickened liquid, a gel, an emulsion, an aqueous/alcoholic lotion, a dispersion, a solid bar or an aerosol foam.

17. Composition according to claim 1, wherein further containing additives chosen from foam reinforcers, sequestering agents, electrolytes, fragrances, preservatives, fatty alcohols, mineral, vegetable or animal oils, mineral, vegetable, animal or synthetic waxes, ceramides, UV screening agents, pearlescence agents, agents for combating free radicals, biocides, antibacterials, antidandruff, antiseborrheic or antiparasitic agents, repellents, dyes, pigments, oxidizing agents, reducing agents, moisturizers, anionic or nonionic polymers, vitamins or α-hydroxy acids.

18. Process for cosmetic washing and/or conditioning of the hair or of the skin, comprising applying an effective amount of composition according to claim 1 to the skin or to the hair, this application optionally being followed by rinsing with water.

* * * * *